US008870814B2

(12) United States Patent
Richard et al.

(10) Patent No.: US 8,870,814 B2
(45) Date of Patent: Oct. 28, 2014

(54) IMPLANTABLE OR INSERTABLE MEDICAL DEVICES CONTAINING SILICONE COPOLYMER FOR CONTROLLED DELIVERY OF THERAPEUTIC AGENT

(75) Inventors: Robert E. Richard, Wrentham, MA (US); Marlene C. Schwarz, Auburndale, MA (US); Frederick H. Strickler, Natick, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2152 days.

(21) Appl. No.: 10/632,008

(22) Filed: Jul. 31, 2003

(65) Prior Publication Data

US 2005/0027283 A1    Feb. 3, 2005

(51) Int. Cl.
| | | |
|---|---|---|
| *A61K 9/22* | (2006.01) | |
| *A61M 37/00* | (2006.01) | |
| *A61L 33/00* | (2006.01) | |
| *A61L 31/10* | (2006.01) | |
| *A61L 31/06* | (2006.01) | |
| *A61L 29/06* | (2006.01) | |
| *A61L 29/08* | (2006.01) | |
| *A61L 31/16* | (2006.01) | |
| *A61L 29/16* | (2006.01) | |
| *A61K 9/00* | (2006.01) | |

(52) U.S. Cl.
CPC ............... *A61K 9/0024* (2013.01); *A61L 31/10* (2013.01); *A61L 31/06* (2013.01); *A61L 2300/602* (2013.01); *A61L 29/06* (2013.01); *A61L 29/085* (2013.01); *A61L 31/16* (2013.01); *A61L 29/16* (2013.01)
USPC ....................... 604/93.01; 604/890.1; 427/2.1

(58) Field of Classification Search
USPC ......................................... 604/890.1; 427/2.1
See application file for complete search history.

(56) References Cited

U.S. PATENT DOCUMENTS

| | | | | |
|---|---|---|---|---|
| 3,896,819 | A * | 7/1975 | Zaffaroni et al. ............. 128/833 |
| 4,230,686 | A * | 10/1980 | Schopflin et al. ............. 424/425 |
| 4,254,248 | A | 3/1981 | Friends et al. ................. 526/279 |
| 4,559,054 | A * | 12/1985 | Bruck ............................ 424/424 |
| 4,584,356 | A * | 4/1986 | Crivello ........................ 525/479 |
| 4,616,064 | A * | 10/1986 | Zukosky et al. ............. 525/92 B |
| 4,677,169 | A | 6/1987 | Crivello ........................ 525/479 |
| 4,833,218 | A * | 5/1989 | Lee ............................... 525/455 |
| 4,946,899 | A | 8/1990 | Kennedy et al. ............. 525/244 |
| 5,019,096 | A * | 5/1991 | Fox et al. ........................ 600/36 |
| 5,057,619 | A * | 10/1991 | Kumar et al. ................. 556/420 |
| 5,200,436 | A | 4/1993 | Kumar et al. .................... 522/57 |
| 5,258,020 | A | 11/1993 | Froix ............................... 623/1 |
| 5,304,121 | A | 4/1994 | Sahatjian ........................ 604/53 |
| 5,430,121 | A * | 7/1995 | Pudleiner et al. ............... 528/28 |
| 5,512,650 | A | 4/1996 | Leir et al. ........................ 528/14 |
| 5,616,608 | A | 4/1997 | Kinsella et al. ............... 514/449 |
| 5,639,810 | A * | 6/1997 | Smith, III et al. ............. 524/269 |
| 5,716,981 | A | 2/1998 | Hunter et al. ................. 514/449 |
| 5,733,925 | A | 3/1998 | Kunz et al. ................... 514/449 |
| 5,741,331 | A | 4/1998 | Pinchuk .......................... 623/11 |
| 5,772,640 | A | 6/1998 | Modak et al. ................. 604/265 |
| 5,837,313 | A * | 11/1998 | Ding et al. ................... 427/2.21 |
| 5,856,367 | A | 1/1999 | Barrows et al. ................. 521/64 |
| 5,879,697 | A | 3/1999 | Ding et al. .................... 424/422 |
| 5,954,706 | A | 9/1999 | Sahatjian ...................... 604/509 |
| 6,099,562 | A | 8/2000 | Ding et al. ................... 623/1.46 |
| 6,102,898 | A | 8/2000 | Khan et al. ................... 604/265 |
| 6,280,411 | B1 | 8/2001 | Lennox .................... 604/103.05 |
| 6,284,856 | B1 * | 9/2001 | Lee ............................. 526/329.2 |
| 6,335,029 | B1 * | 1/2002 | Kamath et al. ............... 424/423 |
| 6,545,097 | B2 * | 4/2003 | Pinchuk et al. ............... 525/240 |
| 6,663,668 | B1 * | 12/2003 | Chaouk et al. ............... 623/5.16 |
| 6,794,464 | B2 * | 9/2004 | Jukarainen et al. ........... 525/474 |
| 6,887,948 | B2 * | 5/2005 | Jukarainen et al. ........... 525/474 |
| 6,896,842 | B1 * | 5/2005 | Hamilton et al. ............. 264/515 |
| 2001/0024661 | A1 | 9/2001 | Modak et al. ................. 424/486 |
| 2002/0045706 | A1 | 4/2002 | Houston et al. ............... 525/100 |
| 2002/0107330 | A1 | 8/2002 | Pinchuk et al. ............... 525/242 |

FOREIGN PATENT DOCUMENTS

| | | | |
|---|---|---|---|
| EP | 0413550 A3 | 2/1991 | |
| GB | 1 580 128 | 11/1980 | ............. C08G 77/48 |
| JP | 54-135495 | 10/1979 | |
| WO | 9503354 | 2/1995 | |
| WO | 9725085 | 7/1997 | |
| WO | WO 02/47731 A2 | 6/2002 | |
| WO | WO 2004/000380 A1 | 12/2003 | ............. A61L 27/34 |

OTHER PUBLICATIONS

Liping Tang et al., "Anti-inflammatory Properties of Triblock Siloxane Copolymer-Blended Materials," *Biomaterials*, vol. 20, 1999, pp. 1365-1370.

Salamone, Joseph C., ed., *Concise Polymeric Materials Encyclopedia* (Boca Raton, FL: CRC Press, 1999), pp. 812-814.

James F. Beecher et al., "Morphology and Mechanical Behavior of Block Polymers," *Journal of Polymer Scienc*, Part C, No. 26 (1969), pp. 117-134.

(Continued)

*Primary Examiner* — Scott Long
*Assistant Examiner* — Sarah Alawadi
(74) *Attorney, Agent, or Firm* — Fish & Richardson P.C.

(57) ABSTRACT

Implantable or insertable medical devices are described. The medical devices comprise (a) a therapeutic agent and (b) a polymeric release region, which controls the release of the therapeutic agent upon administration to a patient. The polymeric release region further comprises a silicone copolymer that contains a plurality of siloxane units and a plurality of non-siloxane units. Also described are methods for administering a therapeutic agent to a patient using the above implantable or insertable medical devices as well as methods of making the above devices.

27 Claims, No Drawings

(56) References Cited

OTHER PUBLICATIONS

Kohtaro Kimishima et al., "Control of Self-Assembled Structures in Binary Mixtures of A-B Diblock Copolymer and A-C Diblock Copolymer by Changing the Interaction Between B and C Block Chains," *Macromolecules*, 32 (1999), pp. 2585-2596.

Richard J. Spontak et al., "Phase Behavior of Ordered Diblock Copolymer Blends: Effect of Compositional Heterogeneity," *Macromolecules*, 29 (1996), pp. 4494-4507.

Hong G. Jeon et al., "Microphase and Macrophase Transitions in Binary Blends of Diblock Copolymers," *Macromolecules*, 32 (1999), pp. 1803-1808.

Steven K. Pollack et al., "Siloxane/Styrene Copolymers via Nitroxide-Mediated Radical Polymerization," *ACS Polymer Preprints*, 40 (2), pp. 370-371 (1999).

Richard G. Jones et al., "A Convenient Route to Poly(methylphenylsilane)—*Graft*-Polystyrene Copolymers," *Macromol. Chem. Phys.*, 198 (1997), pp. 3571-3579.

* cited by examiner

US 8,870,814 B2

IMPLANTABLE OR INSERTABLE MEDICAL DEVICES CONTAINING SILICONE COPOLYMER FOR CONTROLLED DELIVERY OF THERAPEUTIC AGENT

FIELD OF THE INVENTION

The present invention relates to implantable or insertable medical devices for controlled delivery of one or more therapeutic agents.

BACKGROUND OF THE INVENTION

Numerous medical devices have been developed for the delivery of therapeutic agents to the body.

In accordance with some delivery strategies, a therapeutic agent is provided (a) within a polymeric carrier layer and/or (b) beneath a polymeric barrier layer that is associated with an implantable or insertable medical device. Once the medical device is placed at the desired location within a patient, the therapeutic agent is released from the medical device at a rate that is dependent upon the nature of the polymeric carrier and/or barrier layer.

The desired release profile for the therapeutic agent is dependent upon the particular treatment at hand, including the specific condition being treated, the specific therapeutic agent selected, the specific site of administration, and so forth. Accordingly, there is a continuing need for polymeric materials that can serve as release regions, such as barrier layers and/or carrier layers, which are able to provide a range of therapeutic agent release rates.

SUMMARY OF THE INVENTION

The present invention is directed to novel implantable or insertable medical devices, which provide controlled release of a therapeutic agent.

According to a first aspect of the present invention, an implantable or insertable medical device is provided, which comprises (a) a therapeutic agent and (b) a polymeric release region that controls the release of the therapeutic agent upon administration to a patient. The polymeric release region comprises a silicone copolymer, which contains a plurality of siloxane units and a plurality of non-siloxane units. The non-siloxane units can be, for example, low or elevated $T_g$ non-siloxane units. The elevated Tg non-siloxane units of the silicone copolymer can correspond, for example, to vinyl monomers, aromatic monomers, methacrylic monomers, acrylic monomers and/or alkene monomers. The low Tg non-siloxane units of the silicone copolymer can correspond, for example, acrylic monomers, methacrylic monomers, vinyl ether monomers, cyclic ether monomers, ester monomers, unsaturated hydrocarbon monomers, and/or halogenated unsaturated hydrocarbon monomers.

The polymeric release region of the implantable or insertable medical device can be, for example, (a) a carrier region that comprises the therapeutic agent or (b) a barrier region that is disposed over a therapeutic-agent-containing region that comprises the therapeutic agent. In certain embodiments, the polymeric release region is in the form of a coating layer.

Where elevated $T_g$ non-siloxane units are selected, the silicone copolymer beneficially has a first glass transition temperature that is greater than ambient temperature and a second glass transition temperature that is less than ambient temperature.

The silicone copolymer can be, for example, a block copolymer that comprises (a) one or more blocks of siloxane units and (b) one or more blocks of elevated $T_g$ non-siloxane units. The block(s) of siloxane units can correspond, for example, to a rubbery phase within the release region at ambient temperatures, while the block(s) of elevated $T_g$ non-siloxane units can correspond, for example, to a hard phase within the release layer at ambient temperatures. Examples of silicone block copolymers include diblock copolymers, triblock copolymers and graft copolymers.

Examples of implantable or insertable medical device include catheters, guide wires, balloons, filters, stents, stent grafts, vascular grafts, vascular patches, and shunts. The implantable or insertable medical device may be adapted for implantation or insertion into, for example, the coronary vasculature, peripheral vascular system, esophagus, trachea, colon, biliary tract, urinary tract, prostate or brain.

The therapeutic agent can be selected from any number of categories, including anti-thrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, and agents that interfere with endogenous vasoactive mechanisms.

According to another aspect of the present invention, a method of forming the above implantable or insertable medical device is provided. The method comprises (a) providing a solution comprising the silicone copolymer and a solvent (which can comprise one or more solvent species); and (b) forming the release region from the solution by removing the solvent from the solution. Solvent spraying is one beneficial technique for forming the release region. In some embodiments (for example, where a carrier region is formed), the solution can further comprise the therapeutic agent in dissolved or dispersed form. In other embodiments (for example, where a barrier region is formed), the solution is applied over a therapeutic-agent-containing region.

According to another aspect of the present invention, a method is provided for releasing a therapeutic agent within a patient. The method comprises (a) providing an implantable or insertable medical device like that above; (b) implanting or inserting the therapeutic-agent-releasing medical device of into the patient. In certain embodiments, the medical device is inserted into the vasculature, where the therapeutic agent is released for example, in the treatment of restenosis.

One advantage of the present invention is that implantable or insertable medical devices can be provided, which give or result in controlled release of a therapeutic agent.

Another advantage of the present invention is that a variety of materials can be provided, which can be used in release regions of implantable or insertable medical devices.

Another advantage of the present invention is that implantable or insertable medical devices can be provided, which are relatively resistant to the effects of radiation sterilization, particularly where quantities of radiation are used that are effective to kill pathogens.

These and other embodiments and advantages of the present invention will become immediately apparent to those of ordinary skill in the art upon review of the Detailed Description and Claims to follow.

DETAILED DESCRIPTION OF THE INVENTION

The present invention relates to implantable or insertable medical devices that comprise (a) a therapeutic agent and (b) a polymeric release region comprising a silicone copolymer, which release region controls the release of the therapeutic agent upon administration to a patient.

The polymeric release region can be provided in a number of configurations. For example, the polymeric release region can constitute the entirety of the medical device, or it can constitute only a portion of the medical device. The portion of the medical device can be, for example, one or more medical device layers (e.g., one or more coating layers), one or medical device components or portions thereof, and so forth.

By "release region" is meant a region that regulates the rate of release of a therapeutic agent. Release regions are commonly either carrier regions or barrier regions. A "carrier region" is a region which contains at least one therapeutic agent and from which the therapeutic agent is released. A "barrier region" is a region that is disposed between a source of therapeutic agent and a site of intended release, which controls the rate at which the therapeutic agent is released.

For instance, in some embodiments of the present invention, an outer carrier layer, is disposed over at least a portion of an implantable or insertable medical device substrate. Upon implantation or insertion of the device, the therapeutic agent is released from the carrier layer in a controlled fashion. In other embodiments, a therapeutic-agent-containing layer and a barrier layer are provided over at least a portion of an implantable or insertable medical device substrate. Because the barrier layer is disposed over the therapeutic-agent-containing layer, the barrier layer acts to control release of the therapeutic agent from the medical device upon implantation or insertion of the same.

Preferred implantable or insertable medical devices for use in conjunction with the present invention include catheters (for example, renal or vascular catheters such as balloon catheters), guide wires, balloons, filters (e.g., vena cava filters), stents (including coronary vascular stents, cerebral, urethral, ureteral, biliary, tracheal, gastrointestinal and esophageal stents), stent grafts, cerebral aneurysm filler coils (including Guglilmi detachable coils and metal coils), vascular grafts, myocardial plugs, patches, pacemakers and pacemaker leads, heart valves, biopsy devices, or any coated substrate (which can comprise, for example, glass, metal, polymer, ceramic and combinations thereof) that is implanted or inserted into the body, either for procedural use or as an implant, and from which therapeutic agent is released.

The medical devices contemplated for use in connection with the present invention include drug delivery medical devices that are used for either systemic treatment or for the localized treatment of any mammalian tissue or organ. Non-limiting examples are tumors, organs including but not limited to the heart, coronary and peripheral vascular system (referred to overall as "the vasculature"), lungs, trachea, esophagus, brain, liver, kidney, bladder, urethra and ureters, eye, intestines, stomach, pancreas, ovary, and prostate; skeletal muscle; smooth muscle; breast; cartilage; and bone.

One particularly preferred medical device for use in connection with the present invention is a vascular stent that delivers therapeutic agent into the vasculature for the treatment of restenosis. As used herein, "treatment" refers to the prevention of a disease or condition, the reduction or elimination of symptoms associated with a disease or condition, or the substantial or complete elimination a disease or condition. Preferred subjects are mammalian subjects and more preferably human subjects.

As previously noted, the polymeric release region of the present invention comprises a silicone copolymer. A "polymer" is a molecule having one or more chains within which multiple copies of one or more constitutional units are found. A specific example of a polymer is polystyrene

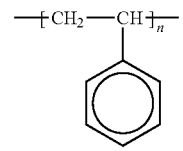

in which n styrene constitutional units are found. A copolymer is a polymer that contains at least two dissimilar constitutional units. A "silicone copolymer" is polymer comprising two or more dissimilar constitutional units, at least one of which is a siloxane unit

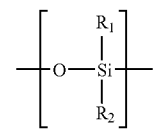

and at least one of which is not. Each of the two or more dissimilar constitutional units is repeated within the molecule, preferably at least 10 times, and more preferably at least 50, 100 or 500 or more times.

In the siloxane unit, $R_1$ and $R_2$ are organic radicals, for example, linear, branched or cyclic alkyl groups (e.g., methyl groups, ethyl groups, propyl groups, isopropyl groups, butyl groups, isobutyl groups, sec-butyl groups, tert-butyl groups, cyclohexyl groups and so forth), which may be substituted or unsubstituted, as well as substituted or unsubstituted aryl groups (e.g., phenyl groups, p-, m- or o-alkyl-substituted phenyl groups and so forth). $R_1$ and $R_2$ can be the same or different.

Such copolymers may include (a) one or more chains containing repeating constitutional units of a single type (e.g., block copolymers), (b) one or more chains containing randomly distributed constitutional units of two or more types (e.g., random copolymers), (c) one or more chains containing two or more constitutional units that repeat within an ongoing series (e.g., alternating copolymers), and so forth.

The copolymers of the present invention may be provided in a variety of configurations, including cyclic, linear and branched configurations. Branched configurations include star-shaped configurations (e.g., configurations in which three or more chains emanate from a single branch point), comb configurations (e.g., graft copolymers having a main chain and a plurality of branching side chains) and dendritic configurations (including arborescent or hyperbranched copolymers).

The silicone copolymers of the present invention typically have an elongation at break of at least 25% at ambient temperature. "Elongation" is an increase in length of a test specimen under tension, stated herein as a percentage of the original length. The "elongation at break" is the amount of elongation that is observed at the point where the specimen breaks or otherwise fails under tension. Ambient temperature is typically 25° C.-45° C., more typically body temperature. (e.g., 35° C.-40° C.).

In some embodiments, the non-siloxane units of the silicone copolymers that are used in connection with the present invention are elevated $T_g$ non-siloxane units. By "elevated $T_g$ non-siloxane unit" is meant a constitutional unit that corresponds to a monomer, which can display either (a) a glass transition temperature ($T_g$), as measured by any of a number of techniques including differential scanning calorimetry (DSC), dynamic mechanical analysis (DMA), or dielectric analysis (DEA), that is above ambient temperature when the monomer is in homopolymer form or (b) a melting point ($T_m$), as measured by any of a number of techniques including differential scanning calorimetry (DSC), dynamic mechanical analysis (DMA), or dielectric analysis (DEA), that is above ambient temperature when the monomer is in homopolymer form.

In some embodiments, the non-siloxane units of the silicone copolymers that are used in connection with the present invention are low $T_g$ non-siloxane units. By "low $T_g$ non-siloxane unit" is meant a constitutional unit that corresponds to a monomer, which can display a glass transition temperature ($T_g$), as measured by any of a number of techniques including those discussed above, that is below ambient temperature when the monomer is polymerized as a homopolymer.

Numerous non-siloxane units can be used in connection with the silicone copolymers of the present invention.

The elevated Tg non-siloxane units can be those that correspond to, for example, vinyl aromatic monomers, other vinyl monomers, other aromatic monomers, methacrylic monomers, acrylic monomers, and alkene monomers.

Vinyl aromatic monomers are those having aromatic and vinyl moieties and include unsubstituted monomers, vinyl-substituted monomers and ring-substituted monomers. Suitable vinyl aromatic monomers include the following (listed along with a published homopolymer $T_g$ and, in some instances, a published homopolymer $T_m$): (a) unsubstituted vinyl aromatics, such as atactic styrene ($T_g$ 100° C.), isotactic styrene ($T_g$ 100° C.) ($T_m$ 240° C.) and 2-vinyl naphthalene ($T_g$ 151° C.), (b) vinyl substituted aromatics such as α-methyl styrene, (c) ring-substituted vinyl aromatics including (i) ring-alkylated vinyl aromatics such as 3-methylsytrene ($T_g$ 97° C.), 4-methylsytrene ($T_g$ 97° C.), 2,4-dimethylsytrene ($T_g$ 112° C.), 2,5-dimethylsytrene ($T_g$ 143° C.), 3,5-dimethylsytrene ($T_g$ 104° C.), 2,4,6-trimethylsytrene ($T_g$ 162° C.), and 4-tert-butylstyrene ($T_g$ 127° C.), (ii) ring-alkoxylated vinyl aromatics, such as 4-methoxysytrene ($T_g$ 113° C.) and 4-ethoxysytrene ($T_g$ 86° C.), (iii) ring-halogenated vinyl aromatics such as 2-chlorosytrene ($T_g$ 119° C.), 3-chlorosytrene ($T_g$ 90° C), 4-chlorosytrene ($T_g$ 110° C.), 2,6-dichlorosytrene ($T_g$ 167° C.), 4-bromostyrene ($T_g$ 118° C.) and 4-fluorostyrene ($T_g$ 95° C.) and (iv) ester-substituted vinyl aromatics such as 4-acetoxystyrene ($T_g$ 116° C.).

Other suitable vinyl monomers include the following: (a) vinyl alcohol ($T_g$ 85° C.) ($T_m$ 220° C.); (b) vinyl esters such as vinyl benzoate ($T_g$ 71° C.), vinyl 4-tert-butyl benzoate ($T_g$ 101° C.), vinyl cyclohexanoate ($T_g$ 76° C.), vinyl pivalate ($T_g$ 86° C.), vinyl trifluoroacetate ($T_g$ 46° C.), vinyl butyral ($T_g$ 49° C.) ($T_m$ 322° C.), (c) vinyl amines such as 2-vinyl pyridine ($T_g$ 104° C.), 4-vinyl pyridine ($T_g$ 142° C.), and vinyl carbazole ($T_g$ 227° C.) ($T_m$ 320° C.), (d) vinyl halides such as vinyl chloride ($T_g$ 81° C.) ($T_m$ 227° C.) and vinyl fluoride ($T_g$ 40° C.) ($T_m$ 171° C.); (e) alkyl vinyl ethers such as methyl vinyl ether ($T_g$ −31° C.) ($T_m$ 144° C.), propyl vinyl ether ($T_g$ −49° C.) ($T_m$ 76° C.), butyl vinyl ether,($T_g$ −55° C.) ($T_m$ 64° C.), isobutyl vinyl ether ($T_g$ −19° C.) ($T_m$ 165° C.), tert-butyl vinyl ether ($T_g$ 88° C.) ($T_m$ 250° C.) and cyclohexyl vinyl ether ($T_g$ 81° C.), and (f) other vinyl compounds such as 1-vinyl-2-pyrrolidone ($T_g$ 54° C.) and vinyl ferrocene ($T_g$ 189° C.).

Suitable aromatic monomers, other than vinyl aromatics, include acenaphthalene ($T_g$ 214° C.) and indene ($T_g$ 85° C.).

Suitable methacrylic monomers include (a) methacrylic acid ($T_g$ 228° C.), (b) methacrylic acid salts such as sodium methacrylate ($T_g$ 310° C.), (c) methacrylic acid anhydride ($T_g$ 159° C.), (d) methacrylic acid esters (methacrylates) including (i) alkyl methacrylates such as atactic methyl methacrylate ($T_g$ 105-120° C.), syndiotactic methyl methacrylate ($T_g$ 115° C.) ($T_m$ 200° C.), ethyl methacrylate ($T_g$ 65° C.), isopropyl methacrylate ($T_g$ 81° C.), isobutyl methacrylate ($T_g$ 53° C.), t-butyl methacrylate ($T_g$ 118° C.) and cyclohexyl methacrylate ($T_g$ 92° C.), (ii) aromatic methacrylates such as phenyl methacrylate ($T_g$ 110° C.) and including aromatic alkyl methacrylates such as benzyl methacrylate ($T_g$ 54° C.), (iii) hydroxyalkyl methacrylates such as 2-hydroxyethyl methacrylate ($T_g$ 57C.) and 2-hydroxypropyl methacrylate ($T_g$ 76° C.), (iv) additional methacrylates including isobornyl methacrylate ($T_g$ 110° C.) and trimethylsilyl methacrylate ($T_g$ 68° C.), and (e) other methacrylic-acid derivatives including methacrylonitrile ($T_g$ 120° C.).

Suitable acrylic monomers include (a) acrylic acid ($T_g$ 105° C.), its anhydride and salt forms, such as potassium acrylate ($T_g$ 194° C.) and sodium acrylate ($T_g$ 230° C.); (b) certain acrylic acid esters such as isopropyl acrylate ($T_g$ −11° C.) ($T_m$ 162° C.), tert-butyl acrylate ($T_g$ 43-107° C.) ($T_m$ 193° C.), hexyl acrylate ($T_g$ 57° C.) and isobornyl acrylate ($T_g$ 94° C.); (c) acrylic acid amides such as acrylamide ($T_g$ 165° C.), N-isopropylacrylamide ($T_g$ 85-130° C.) and N,N dimethylacrylamide ($T_g$ 89° C.); and (d) other acrylic-acid derivatives including acrylonitrile ($T_g$ 125° C.) ($T_m$ 319° C.).

Suitable alkene based monomers include the following: ethylene (HDPE) ($T_g$ −125° C.) ($T_m$ 130° C.), isotactic propylene ($T_g$ −8° C.) ($T_m$ 176° C.), 4-methyl pentene ($T_g$ 29° C.) ($T_m$ 250° C.), 1-octadecene ($T_g$ 55° C.), and tetrafluoroethylene ($T_g$ 117° C.) ($T_m$ 327° C.).

Low Tg non-siloxane units can be those that correspond to, for example, acrylic monomers, methacrylic monomers, vinyl ether monomers, cyclic ether monomers, ester monomers, unsaturated hydrocarbon monomers, halogenated unsaturated hydrocarbon monomers, and other monomers.

Suitable acrylic monomers include (a) alkyl acrylates such as methyl acrylate ($T_g$ 10° C.), ethyl acrylate ($T_g$ −24° C.), propyl acrylate, isopropyl acrylate ($T_g$ −1120 C., isotactic), butyl acrylate ($T_g$ −54° C.), sec-butyl acrylate ($T_g$ −26° C.), isobutyl acrylate ($T_g$ −24° C.), cyclohexyl acrylate ($T_g$ 19° C.), 2-ethylhexyl acrylate,($T_g$ −50° C.), dodecyl acrylate ($T_g$ −3° C.) and hexadecyl acrylate ($T_g$ 35° C.), (b) arylalkyl acrylates such as benzyl acrylate ($T_g$ 6° C.), (c) alkoxyalkyl acrylates such as 2-ethoxyethyl acrylate ($T_g$ −50° C.) and 2-methoxyethyl acrylate ($T_g$ −50° C.), (d) halo-alkyl acrylates such as 2,2,2-trifluoroethyl acrylate ($T_g$ −10° C.) and (e) cyano-alkyl acrylates such as 2-cyanoethyl acrylate ($T_g$ 4° C.).

Suitable methacrylic monomers include (a) alkyl methacrylates such as butyl methacrylate ($T_g$ 20° C.), hexyl methacrylate ($T_g$ −5° C.), 2-ethylhexyl methacrylate ($T_g$ −10° C.), octyl methacrylate ($T_g$ −20° C.), dodecyl methacrylate ($T_g$ −65° C.), hexadecyl methacrylate ($T_g$ 15° C.) and octadecyl methacrylate ($T_g$ −100° C.) and (b) aminoalkyl methacrylates such as diethylaminoethyl methacrylate ($T_g$ 20° C.) and 2-tert-butyl-aminoethyl methacrylate ($T_g$ 33° C.).

Suitable vinyl ether-monomers include (a) alkyl vinyl ethers such as methyl vinyl ether ($T_g$ −31° C.), ethyl vinyl ether ($T_g$ −43° C.), propyl vinyl ether ($T_g$ −49° C.), butyl vinyl ether ($T_g$ −55° C.), isobutyl vinyl ether ($T_g$ −19° C.), 2-ethyl-hexyl vinyl ether ($T_g$ −66° C.) and dodecyl vinyl ether ($T_g$ −62?C).

Suitable cyclic ether monomers include tetrahydrofuran ($T_g$ −84° C.), trimethylene oxide ($T_g$ −78° C.), ethylene oxide ($T_g$ −66° C.), propylene oxide ($T_g$ −75° C.), methyl glycidyl ether ($T_g$ −62° C.), butyl glycidyl ether ($T_g$ −79° C.), allyl glycidyl ether ($T_g$ −78° C.), epibromohydrin ($T_g$ −14° C.), epichlorohydrin ($T_g$ −22° C.), 1,2-epoxybutane ($T_g$ −70° C.), 1,2-epoxyoctane ($T_g$ −67° C.) and 1,2-epoxydecane ($T_g$ −70° C.).

Suitable ester monomers (other than acrylates and methacrylates) include ethylene malonate ($T_g$ −29° C.), vinyl acetate ($T_g$ 30° C.), and vinyl propionate ($T_g$ 10° C.).

Suitable unsaturated hydrocarbon monomers include ethylene, propylene ($T_g$ −8 to −13° C.), isobutylene ($T_g$ −73° C.), 1-butene ($T_g$ −24° C.), trans-butadiene ($T_g$ −58° C.), 4-methyl pentene ($T_g$ 29° C.), 1-octene ($T_g$ −63° C.) and other α-olefins, cis-isoprene ($T_g$ −63° C.), and trans-isoprene ($T_g$ −66° C.).

Suitable halogenated unsaturated hydrocarbon monomers include vinylidene chloride ($T_g$ −18° C.), vinylidene fluoride ($T_g$ −40° C.), cis-chlorobutadiene ($T_g$ −20° C.), and trans-chlorobutadiene ($T_g$ −40° C.).

Suitable additional monomers include ε-caprolactone ,($T_g$ −60° C.).

In many embodiments, the copolymers will comprise (a) one or more polysiloxane chains that result in the formation of a rubbery phase within the release region at ambient temperatures and (b) one or more elevated $T_g$ non-siloxane chains that result in the formation of a hard phase within the release region at ambient temperatures.

Some exemplary copolymers are block copolymers comprising (a) one or more polysiloxane (silicone) blocks (e.g., one or more blocks of polydimethylsiloxane ($T_g$ −127° C.) ($T_m$ −40° C.), polydiethylsiloxane, polymethylethylsiloxane, polymethylphenylsiloxane ($T_g$ −86° C.), and/or polydiphenylsiloxane) and (b) one or more blocks of elevated Tg non-siloxane units such as those listed above.

One preferred group of block copolymers has (a) a silicon midblock or main chain, which can be for example, a block of polydimethylsiloxane, polymethylphenylsiloxane or polydiphenylsiloxane having a linear, star or branched configuration, and (b) one or more elevated $T_g$ endblocks or side chains, which can be for example blocks of polystyrene or poly(alkyl methacrylate).

Two particularly preferred copolymers are: (a) graft copolymers having a silicone main chain and polystyrene side chains, and (b) triblock copolymers having a silicone midblock and a polystyrene endblocks.

The latter are similar in some ways to known polystyrene-polyisobutylene-polystyrene triblock copolyiners (SIBS copolymers), such as are described in U.S. Patent Application 20020107330 and U.S. Pat. No. 6,545,097 entitled "Drug delivery compositions and medical devices containing block copolymer", in that both polymers are thermoplastic elastomers having an elastomeric center block and phase separated, hard polystyrene end blocks.

Implantable or insertable medical devices are typically sterilized by exposure to ethylene oxide or to radiation such as gamma or electron beam radiation. Certain therapeutic agents, however, are unstable under ethylene oxide sterilization conditions. On the other hand, radiation sterilization can lead to chain scission and/or crosslinking of polymers within the medical device, leading to changes in the chemical, physical, and drug-eluting properties of the polymers. For instance, radiation can lead to an unacceptable increase in the surface tack of the material, which can in turn cause defects in the polymer if it is expanded (e.g., when it is in the form of a coating on the surface of an expandable stent or balloon). Silicone blocks, while not being completely immune to radiation damage, are significantly less susceptible to radiation damage than are polyisobutylene blocks, which are known to undergo chain scission during irradiation, especially at the radiation levels used for medical device sterilization (e.g., about 2.5 Mrad). Hence, in this embodiment of the present invention, a material is provided, which has properties that are analogous to SIBS copolymers, while also exhibiting improved immunity to radiation-based changes in polymer properties. The polystyrene-silicone-polystyrene copolymers in this embodiment of the invention are also believed to exhibit outstanding biocompatibility, due to the biocompatibility of the silicone and polystyrene blocks that make up the copolymer.

The silicone copolymers of the present invention can be synthesized using a variety of synthesis schemes. For example, a silicone copolymer can be prepared using hydrosylation chemistry by reacting a dihydride-terminated poly(dimethylsiloxane) with a methacrylate-terminated poly (styrene) in the presence of a platinum catalyst along the following lines:

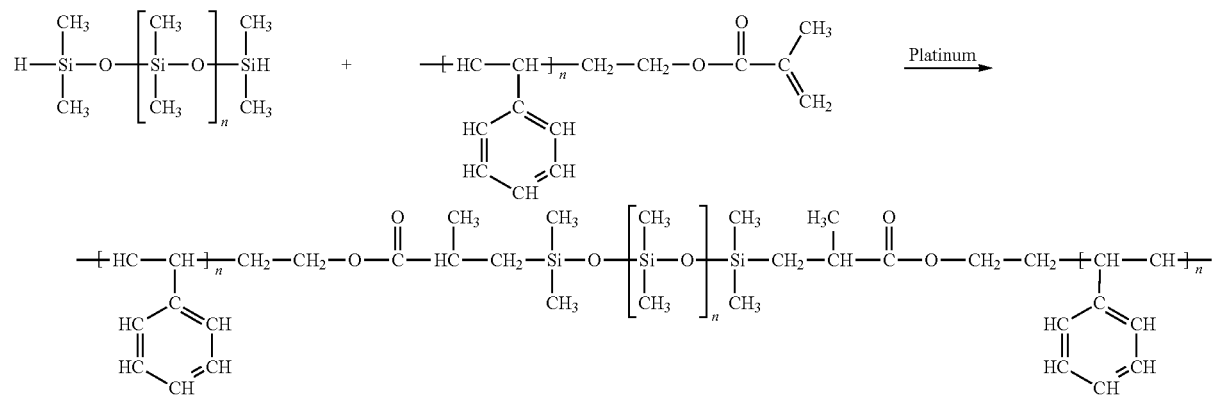

A similar reaction scheme can be used to construct a silicone copolymer having polystyrene grafts along the following lines (only a single polystyrene graft is illustrated):

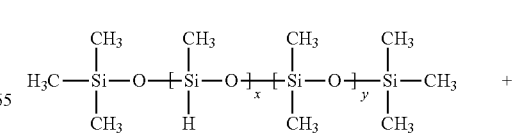

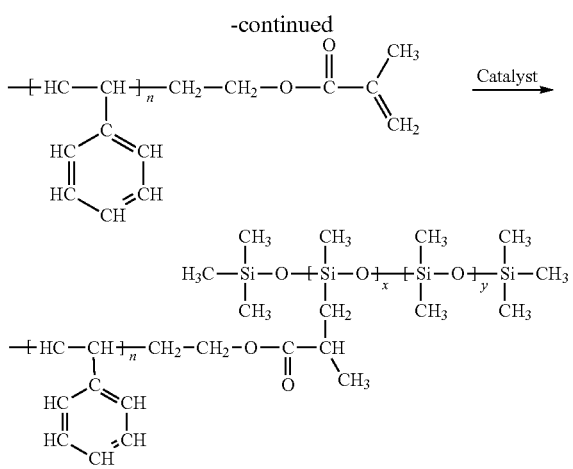

Of course, other reaction chemistries are suitable for the practice of the present invention besides platinum-catalyzed hydrosylation chemistries, for instance, cationic polymerization, anionic polymerization, Ziegler-Natta polymerization, metallocene polymerization, free-radical polymerization, nitroxide-mediated polymerization (NMP), atom transfer radical polymerization (ATRP), and reversible addition-fragmentation chain transfer (RAFT) polymerization chemistries.

For example, a silicone block can be provided with terminal unsaturation (e.g., a terminal vinyl group). At the same time, a non-siloxane block can also be provided with terminal unsaturation (e.g., a terminal vinyl or methacrylate group). The silicone and non-silicone blocks can then be linked using one of the above reaction chemistries.

As a more specific example, a linear, star-shaped or dendritic copolymer can be formed by reacting (a) a linear, star-shaped or dendritic silicone block, whose end groups are unsaturated, with (b) a linear non-siloxane block having a single unsaturated end group. The reaction can be conducted using, for example, a metallocene catalyst.

Siloxane/styrene diblock copolymers have reportedly been synthesized via NMP. See S. K. Pollack, D. U. Singer and A. M. Morgan, "Siloxane/Styrene Diblock Copolymers via Nitroxide Mediated Radical Polymerization", *ACS Polymer Preprints*, 40(2), 370, (1999).

Graft copolymers can also be constructed, for example, by (a) reacting a silicone block having terminal unsaturation with a non-siloxane block having a number of unsaturated side groups, (b) reacting a non-siloxane block having terminal unsaturation with a silicone block having a number of unsaturated side groups, and (c), reacting a silicone block having terminal unsaturation with an unsaturated monomer (thus polymerizing the non-siloxane main chain in situ).

Poly(methylphenylsilane)-graft-poly(styrene) has reportedly been synthesized via ATRP, where bromomethylated poly(methylphenylsilane) is utilized as a macromolecular initiator in an ATRP of styrene. See S. J. Holder et al., "A convenient route to poly(methylphenylsilane)-graft-polystyrene copolymers," *Macromol. Chem. Phys.*, 1997, vol. 198, p. 3571.

Once the silicone copolymer is provided, numerous techniques are available for forming the polymeric release regions of the present invention. For example, where the selected copolymer has thermoplastic characteristics, a variety of standard thermoplastic processing techniques can be used to form the polymeric release region, including compression molding, injection molding, blow molding, spinning, vacuum forming and calendaring, as well as extrusion into sheets, fibers, rods, tubes and other cross-sectional profiles of various lengths.

Using these and other techniques, entire devices or portions thereof can be made. For example, an entire stent can be extruded using the above techniques. As another example, a coating can be provided by extruding a coating layer onto a pre-existing stent. As yet another example, a coating can be co-extruded along with an underlying stent body.

If the therapeutic agent is stable at processing temperatures, then it can be combined with the copolymer prior to thermoplastic processing, producing a therapeutic-agent containing carrier region. If not, then a carrier region can nonetheless be formed by subsequent introduction of therapeutic agent as discussed below.

Polymeric release regions can also be formed using solvent-based techniques in which copolymer is first dissolved or dispersed in a solvent and the resulting mixture is subsequently used to form the polymeric release region.

Where solvent-based techniques are used, the solvent system that is selected will contain one or more solvent species. The solvent system preferably is a good solvent for the copolymer and, where included, for the therapeutic agent as well. The particular solvent species that make tip the solvent system may also be selected based on other characteristics including drying rate and surface tension.

Preferred solvent-based techniques include, but are not limited to, solvent casting techniques, spin coating techniques, web coating techniques, solvent spraying techniques, dipping techniques, techniques involving coating via mechanical suspension including air suspension, ink jet techniques, electrostatic techniques, and combinations of these processes.

Typically, a mixture containing solvent and copolymer is applied to a substrate to form a release region. For example, the substrate can be all or a portion of an implantable or insertable medical device, such as a stent, to which a release layer is applied.

On the other hand, the substrate can also be, for example, a template from which the polymeric release region is removed after solvent elimination. Such template-based techniques are particularly appropriate for forming simple objects such as sheets, tubes, cylinders and so forth, which can be easily removed from a template substrate.

In other techniques, for example, fiber forming techniques, the polymeric release region is formed without the aid of a substrate or template.

Where appropriate, techniques such as those listed above can be repeated or combined to build up a release layer to a desired thickness. The thickness of the release layer can be varied in other ways as well. For example, in one preferred process, solvent spraying, coating thickness can be increased by modification of coating process parameters, including increasing spray flow rate, slowing the movement between the substrate to be coated and the spray nozzle, providing repeated passes and so forth.

Where a carrier region is formed (as opposed to, for example, a barrier region), a therapeutic agent can be dissolved or dispersed in the copolymer/solvent mixture if desired, and hence co-established with the carrier region. In other embodiments, on the other hand, the therapeutic agent can be dissolved or dispersed within a solvent, and the resulting solution contacted with a polymer region that is previously formed using, for example, one or more of the application techniques described above (e.g., dipping, spraying, etc.).

Barrier layers, on the other hand, are formed over a therapeutic-agent-containing region, for example, using solvent-based techniques such as those discussed above, wherein barrier polymer(s) is first dissolved or dispersed in a solvent, and the resulting mixture is subsequently used to form the barrier layer. In some embodiments, the therapeutic-agent-containing region will comprise one or more polymers, which can be selected, for example, from the polymers listed herein. As such, the therapeutic-agent-containing region can also be established using solvent-based techniques (e.g., dipping, spraying, etc.) such as those discussed above. In other embodiments, the therapeutic-agent-containing region beneath the barrier layer is established without an associated polymer. In this case, the therapeutic agent can simply be dissolved or dispersed in a solvent or liquid, and the resulting solution/dispersion can be contacted with a substrate again using, for instance, one or more of the above-described application techniques.

Where the release region is formed using a solvent-based technique, it is preferably dried after application to remove the solvents. The release region typically further conforms to any underlying surface during the drying process.

The medical devices of the present invention are typically sterilized using conventional processes such as exposure to ethylene oxide or radiation such as gamma or electron beam radiation. Certain therapeutic agents, however, are unstable under ethylene oxide sterilization conditions. In such cases, radiation sterilization is typically used, in which case chain scission and/or crosslinking of the silicone copolymer is addressed, either by taking into account the chemical and physical property changes that occur or by selecting a silicone copolymer that is relatively resistant to radiation sterilization.

The release profile associated with the release region can be modified in a number of ways, including (a) changing the type of siloxane unit(s) and/or non-siloxane unit(s) within the copolymer, (b) changing the ratio of siloxane unit(s) to non-siloxane unit(s) within the copolymer, (c) changing the molecular weight of the copolymer, (d) changing the distribution of the siloxane and non-siloxane units within the copolymer (e.g., a block copolymer vs. a random copolymer vs. an alternating copolymer) and/or (e) changing the configuration of the polymer (e.g., a linear copolymer vs. a branched copolymer).

For example, the release profile of the therapeutic agent can be modified by increasing or decreasing the overall hydrophilicity of the copolymer (or, viewed conversely, decreasing or increasing the overall hydrophobicity). As a specific example, the hydrophilicity of a block copolymer containing one or more silicone blocks and one or more polystyrene blocks can be increased by replacing at least some of the polystyrene blocks (which are substantially hydrophobic) with blocks of a substantially hydrophilic material such as poly(1-vinyl-2-pyrrolidone).

The release profile can also be modified by varying the thickness of the release region. Moreover, multiple release regions can be employed to modify the release profile. In addition, where a carrier region is employed, a therapeutic-agent concentration gradient can be established within the carrier region to control release of therapeutic agent.

The release profile associated with the release region can also be modified by blending one or more supplementary polymers with the silicone copolymer within the release region, or by providing a separate barrier layer that contains one or more, supplementary polymers. For example, supplementary polymer(s) can be selected and blended into the release region to vary the overall hydrophilicity of the same.

The supplementary polymers may be, for example, homopolymers or copolymers, crosslinked or uncrosslinked, linear or branched, natural or synthetic, thermoplastic or thermosetting. Supplementary polymers include the following: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydoxyalkyl celluloses; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers and copolymers including nylon 6,6, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, polystyrenes, styrene-maleic anhydride copolymers, styrene-butadiene copolymers, styrene-ethylene-butylene copolymers (e.g., a polystyrene-polyethylene/butylene-polystyrene (SEBS) copolymer, available as Kraton® G series polymers), acrylonitrile-styrene copolymers, acrylonitrile-butadiene-styrene copolymers, styrene-butadiene copolymers and styrene-isobutylene copolymers (e.g., polyisobutylene-polystyrene block copolymers such as SIBS), polyvinyl ketones, polyvinylcarbazoles, and polyvinyl esters such as polyvinyl acetates; polybenzimidazoles; ionomers; polyalkyl oxide polymers and copolymers including polyethylene oxides (PEO); glycosaminoglycans; polyesters including polyethylene terephthalates and aliphatic polyesters such as polymers and copolymers of lactide (which includes lactic acid as well as d-,l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; polyurethanes; p-xylylene polymers; polyiminocarbonates; copoly(ether-esters)such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as blends and copolymers of the above.

Medical devices having a sustained release profile are preferred in many cases. By "sustained release profile" is meant a release profile in which less than 25% of the total release from the medical device that occurs over the course of implantation/insertion in the body occurs within the first 1, 2, 3 or even more days of administration. Conversely, this means that more than 75% of the total release from the medical device will occur in a controlled fashion after the device has been implanted/inserted for the same period.

The release characteristics that are ultimately of interest are of course the release characteristics within the subject, for example, within a mammalian subject. However, it is well known in the art to test the release characteristics within an experimental system that gives a good indication of the actual release characteristics within the subject. For example, aqueous buffer systems are commonly used for testing release of therapeutic agents from vascular devices.

"Therapeutic agents","pharmaceutically active agents", "pharmaceutically active materials","drugs" and other related terms may be used interchangeably herein and include genetic therapeutic agents, non-genetic therapeutic agents and cells. Therapeutic agents may be used singly or in combination.

Exemplary non-genetic therapeutic agents for use in connection with the present invention include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promoters; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; and (o)agents that interfere with endogenous vasoactive mechanisms.

Exemplary genetic therapeutic agents for use in connection with the present invention include anti-sense DNA and RNA as well as DNA coding for: (a) anti-sense RNA, (b) tRNA or rRNA to replace defective or deficient endogenous molecules, (c) angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include (a) plasmids, (b) viral vectors such as adenovirus, adenoassociated virus and lentivirus, and (c) non-viral vectors such as lipids, liposomes and cationic lipids.

Cells for use in connection with the present invention include cells of human origin (autologous or allogeneic), including stem cells, or from an animal source (xenogeneic), which can be genetically engineered, if desired, to deliver proteins of interest.

Numerous therapeutic agents, not necessarily exclusive of those listed above, have been identified as candidates for vascular treatment regimens, for example, as agents targeting restenosis. Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway, agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) ACE inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C, and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, paclitaxel and epothilone), caspase activators, proteasome inhibitors, angiogenesis inhibitors (e.g., endostatin, angiostatin and squalamine), rapamycin, cerivastatin, flavopiridol and suramin; (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Numerous additional therapeutic agents useful for the practice of the present invention are also disclosed in U.S. Pat. No. 5,733,925 assigned to NeoRx Corporation, the entire disclosure of which is incorporated by reference.

A wide range of therapeutic agent loadings can be used in connection with the medical devices of the present invention, with the amount of loading being readily determined by those of ordinary skill in the art and ultimately depending, for example, upon the condition to be treated, the nature of the therapeutic agent itself, the means by which the therapeutic agent is administered to the intended subject, and so forth.

The invention is further described with reference to the following non-limiting Example.

EXAMPLE

Synthesis and Characterization of Polydimethylsiloxane-Graft-Polystyrene Copolymer and Polystyrene-Polydimethylsiloxane-Polystyrene Triblock Copolymer Polydimethylsiloxane-co-polystyrene graft and triblock copolymers are thermoplastic elastomers where the polydimethylsiloxane segments are elastomeric and the polystyrene chains form physical crosslinks. The synthesis of these copolymers involves two steps. The first step involves synthesizing a polydimethylsiloxane macroinitiator. The triblock copolymer can be synthesized by reacting a hydride-terminated polydimethylsiloxane with vinyl benzyl chloride. This leaves a benzyl chloride group at both chain ends. The graft copolymer is synthesized from a macroinitiator made from vinyl benzyl chloride and a polydimethylsiloxane-co-polymethylhydrogen siloxane. In this case, the benzyl chloride groups are located along the polymer backbone. These polydimethylsiloxane macroinitiators can then be used to polymerize styrene monomer using atom transfer radical polymerization (ATRP). The polystyrene chains will grow from the benzyl chloride initiating groups located on the polymer chain. The molecular weight of the polystyrene chains can be controlled using ATRP.

Macroinitiator synthesis. Inhibitor is removed from vinyl benzylchloride (m,p isomers) by passing the vinyl benzylchloride through an inhibitor removal column, (Aldrich—306312). The vinyl benzylchloride is collected in a tared vial. A two neck round bottom flask is charged with polydimethylsiloxane-co-polymethylhydrogensiloxane (MW=1,600, 25-30 mol % methylhydrogen siloxane), vinyl benzylchloride, toluene, and platinum catalyst (i.e., platinum-divinyltetramethyldisiloxane complex). The round bottom flask is also equipped with a stopcock. The flask is fitted with a magnetic stir bar, thermometer and reflux condenser, and the reaction mixture is stirred until the polystyrene dissolves. The solution is heated to 50° C. for one hour. The reaction is conducted under air. The solution is allowed to cool to room temperature and is precipitated into ethanol. The extent of reaction is determined by the disappearance of the silicone-hydride bond at 2158 cm$^{-1}$ using FT-IR. A benzyl chloride-terminated polydimethylsiloxane macroinitiator is synthesized by the same procedure except that hydride-terminated polydimethylsiloxane (MW=62,000) is used. A benzyl chloride-grafted polydimethylsiloxane macroinitiator is synthesized by the same procedure except that polydimethylsiloxane-co-polymethylhydrogen siloxane (0.5-1.0 mol % polymethylhydrogen siloxane (MW=55,000)) is used.

Copolymer synthesis. Inhibitor is removed from styrene by passing the styrene through a column of neutral alumina (Aldrich—199974). The styrene is collected in a tared vial. A two neck round bottom flask is fitted with a magnetic stir bar, thermometer and reflux condenser. The flask is charged with macroinitiator (see above), styrene, copper (I) chloride, and 4,4'-dinonyl-2,2'- bipyridine. The round bottom flask is also equipped with a stopcock. The reaction mixture is stirred until it turns dark red in color, after which the solution is sparged with nitrogen for thirty minutes. The reaction solution is heated to 130° C., and the reaction is allowed to proceed for twenty hours. The solution is then allowed to cool below 80° C. before adding toluene to dilute the polymer. Upon exposure to air the reaction solution turns green in color. The polymer solution is cooled to room temperature and passed through a column of neutral alumina to remove the metal complex. The polymer solution is then precipitated into ethanol and the polymer precipitate is filtered.

Stent coatings. Solutions are provided that contain 5 wt % tetrahydrofuran (THF), 94 wt % toluene, 0.25 wt % paclitaxel and 0.75 wt % polymer. All solutions are prepared by mixing the polymer with the toluene and heating to 70° C. for about an hour, cooling to room temperature, adding the THF, adding the paclitaxel, thoroughly mixing (e.g., overnight), and filtering. The following solutions are made: (1) a solution containing 0.75 wt % polystyrene-polydimethylsiloxane-polystyrene triblock copolymer, (2) a solution containing 0.75 wt % polydimethylsiloxane-graft-polystyrene copolymer, and (3) a solution containing 0.75 wt % polystyrene-polyisobutylene-polystyrene triblock copolymer (SIBS), as described in U.S. Patent Application 20020107330 and U.S. Pat. No. 6,545,097 entitled "Drug delivery compositions and medical devices containing block copolymer,"

Solutions are also provided that contain 5 wt % tetrahydrofuran (THF), 94 wt % toluene, 0.10 wt % paclitaxel and 0.90 wt % polymer. All solutions are prepared by mixing the polymer with the toluene and heating to 70° C. for about an hour, adding the THF, adding the paclitaxel, thoroughly mixing (e.g., overnight), and filtering. The following solutions are made: (1) a solution containing 0.90 wt % polystyrene-polydimethylsiloxane-polystyrene triblock copolymer, (2) a solution containing 0.90 wt % polydimethylsiloxane-graft-polystyrene copolymer, (3) a solution containing 0.90 wt % SIBS., Each solution is then placed in a syringe pump and fed to a spray nozzle. A stent is mounted onto a holding device parallel to the nozzle and rotated to ensure uniform coverage. Depending on the spray equipment used, either the stent or spray nozzle can be moved while spraying such that the nozzle moves along the stent while spraying for one or more passes. After a carrier coating is formed in this fashion, the stent is dried, for example, by placing it in a preheated oven for 30 minutes at 65° C., followed by 3 hours at 70° C. 8 stents are formed in this manner for each of the solutions.

Radiation stability. Polystyrene-polydimethylsiloxane-polystyrene triblock copolymer is subjected to electron beam radiation to evaluate the effect of radiation on the stability of the copolymer. The triblock copolymer is exposed to electron beam radiation at a dose of 25 kilograys. The polydispersity index and the molecular weight of the copolymer, both before and after irradiation, are determined by gel permeation chromatography (GPC) using tetrahydrofuran as the mobile phase. Molecular weight and polydispersity data are summarized in the table below.

| Sample | Mn | PDI |
|---|---|---|
| Triblock copolymer (before irradiation) | 6800 | 6.70 |
| Triblock copolymer (after irradiation) | 6400 | 6.90 |

As can be seen from the above table, there is only a slight reduction in number average molecular (Mn) and a slight increase in polydispersity index (PDI) upon exposure to irradiation. Specifically, a decrease of 5.8% in Mn and an increase of 2.8% in PDI are observed. Accordingly, the triblock copolymer is considered radiation stable.

Although various embodiments are specifically illustrated and described herein, it will be appreciated that modifications and variations of the present invention are covered by the above, teachings and are within the purview of the appended claims without departing from the spirit and intended scope of the invention.

The invention claimed is:

1. An implantable or insertable medical device comprising (a) a therapeutic agent and (b) a polymeric carrier region that comprises said therapeutic agent and which releases said therapeutic agent upon administration to a patient, said polymeric carrier region comprising a silicone block copolymer comprising a plurality of siloxane units and a plurality of non-siloxane units, said block copolymer comprising (i) a block of said siloxane units selected from a polydimethylsiloxane block, a polydiethylsiloxane block, a polymethylethylsiloxane block and a polymethylphenylsiloxane block and (ii) a block of elevated $T_g$ non-siloxane units, wherein the polymeric carrier region is in the form of a coating layer that covers all or a part of said medical device.

2. The implantable or insertable medical device of claim 1, wherein said implantable or insertable medical device is selected from a catheter, a guide wire, a balloon, a filter, a stent, a stent graft, a vascular graft, a vascular patch and a shunt.

3. The implantable or insertable medical device of claim 1, wherein said implantable or insertable medical device is adapted for implantation or insertion into the coronary vasculature, peripheral vascular system, esophagus, trachea, colon, biliary tract, urinary tract, prostate or brain.

4. The implantable or insertable medical device of claim 1, wherein said therapeutic agent is selected from one or more of the group consisting of anti-thrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, and agents that interfere with endogenous vasoactive mechanisms.

5. The implantable or insertable medical device of claim 1, wherein said silicone copolymer has an elongation at break of at least 25% at ambient temperature.

6. The implantable or insertable medical device of claim 1, wherein said elevated $T_g$ non-siloxane units-are selected from vinyl monomers, aromatic monomers, methacrylic monomers, acrylic monomers and alkene monomers.

7. The implantable or insertable medical device of claim 1, wherein said block of said elevated $T_g$ non-siloxane units is selected from poly(vinyl monomer) blocks, poly(aromatic monomer) blocks, poly(methacrylic monomer) blocks, poly (acrylic monomer) blocks and poly(alkene monomer) blocks.

8. The implantable or insertable medical device of claim 1, wherein said block of said elevated $T_g$ non-siloxane units is selected from substituted and unsubstituted polystyrene blocks.

9. The implantable or insertable medical device of claim 1, wherein said block of said elevated $T_g$ non-siloxane units is selected from substituted and unsubstituted poly(alkyl methacrylate) blocks.

10. The implantable or insertable medical device of claim 1, wherein said block of said elevated $T_g$ non-siloxane units is selected from poly(styrene) blocks, poly(methyl methacrylate) blocks, poly(ethyl methacrylate) blocks, poly(isopropyl methacrylate) blocks, poly(isobutyl methacrylate) blocks, poly(t-butyl methacrylate) blocks and poly(cyclohexyl methacrylate) blocks.

11. The implantable or insertable medical device of claim 1, wherein said block of said elevated $T_g$ non-siloxane units comprise monomers selected from unsubstituted vinyl aromatics, vinyl substituted aromatics, ring-substituted vinyl aromatics, vinyl monomers, aromatic monomers, methacrylic monomers, acrylic monomers and alkene based monomers.

12. The implantable or insertable medical device of claim 11, wherein said elevated $T_g$ non-siloxane units have a Tg that is greater than 75° C. and said siloxane units have a Tg less than 0° C.

13. The implantable or insertable medical device of claim 1, wherein said polymeric carrier region further comprises a supplemental polymer selected from
 a) polycarboxylic acid polymers and copolymers;
 b) acetal polymers and copolymers;
 c) acrylate and methacrylate polymers and copolymers;

d) cellulosic polymers and copolymers;
e) polyoxymethylene polymers and copolymers;
f) polyimide polymers and copolymers;
g) polysulfone polymers and copolymers;
h) polyamide polymers and copolymers;
i) resins selected from alkyd resins, phenolic resins, urea resins, melamine resins, epoxy resins, allyl resins and epoxide resins;
j) polycarbonates;
k) polyacrylonitriles;
l) polyvinylpyrrolidones;
m) polymers and copolymers of vinyl monomers and which are selected from polyvinyl alcohols, polyvinyl halides, ethylene-vinylacetate copolymers (EVA), polyvinylidene chlorides, polyvinyl ethers, polystyrenes, styrene-maleic anhydride copolymers, styrene-butadiene copolymers, styrene-ethylene-butylene copolymers, acrylonitrile-styrene copolymers, acrylonitrile-butadiene-styrene copolymers, styrene-butadiene copolymers and styrene-isobutylene copolymers, polyvinyl ketones, polyvinylcarbazoles, and polyvinyl esters;
n) polybenzimidazoles;
o) ionomers;
p) polyalkyl oxide polymers and copolymers;
q) glycosaminoglycans;
r) polyesters selected from polyethylene terephthalates and aliphatic polyesters;
s) polyether polymers and copolymers selected from polyarylethers, polyether ketones, and polyether ether ketones;
t) polyphenylene sulfides;
u) polyisocyanates;
v) polyolefin polymers and copolymers selected from polypropylenes, polyethylenes (low and high density, low and high molecular weight), polybutylenes, poly-4-methyl-pen-1-enes, ethylene-alpha-olefin copolymers, ethylene-methyl methacrylate copolymers and ethylene-vinyl acetate copolymers;
w) fluorinated polymers and copolymers selected from polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF);
x) silicone polymers and copolymers;
y) polyurethanes;
z) p-xylylene polymers;
aa) polyiminocarbonates;
bb) copoly(ether-esters) selected from polyethylene oxide-polylactic acid copolymers;
cc) polyphosphazines;
dd) polyalkylene oxalates;
ee) polyoxaamides and polyoxaesters;
ff) polyorthoesters;
gg) biopolymers selected from polypeptides, proteins, polysaccharides and fatty acids and esters thereof; and
hh) blends and copolymers of the foregoing.

14. The implantable or insertable medical device of claim 1, wherein said block copolymer comprises at least two different types of said elevated $T_g$ non-siloxane units.

15. The implantable or insertable medical device of claim 1, wherein said medical device is sterilized using a quantity of radiation effective to kill pathogens.

16. The implantable or insertable medical device of claim 1, wherein said block of said siloxane units corresponds to a rubbery phase within said carrier region at ambient temperatures, and wherein said block of said elevated $T_g$ non-siloxane units corresponds to a hard phase within said carrier layer at ambient temperatures.

17. The implantable or insertable medical device of claim 1, wherein said block copolymer is selected from a diblock copolymer, a triblock copolymer and a graft copolymer.

18. The implantable or insertable medical device of claim 1, comprising a plurality of said blocks of elevated $T_g$ non-siloxane units as endblocks or as side chains.

19. The implantable or insertable medical device of claim 18, wherein said blocks of elevated $T_g$ non-siloxane units are selected from blocks of polystyrene or poly(alkyl methacrylate).

20. The implantable or insertable medical device of claim 19, wherein said copolymer is a triblock copolymer having said block of said siloxane units as a midblock and polystyrene endblocks.

21. The implantable or insertable medical device of claim 1, wherein said copolymer is a graft copolymer having said block of said siloxane units as a main chain and polystyrene side chains.

22. The implantable or insertable medical device of claim 1, wherein the device further comprises a barrier region disposed over the carrier region.

23. The implantable or insertable medical device of claim 1, wherein said polymeric carrier region does not comprise a supplemental polymer.

24. The implantable or insertable medical device of claim 1, wherein said polymeric carrier region does not comprise a supplemental silicone polymer.

25. The implantable or insertable medical device of claim 18, wherein said blocks of elevated $T_g$ non-siloxane units are selected from blocks of polystyrene or poly(methyl methacrylate).

26. The implantable or insertable medical device of claim 18, wherein said blocks of elevated $T_g$ non-siloxane units are polystyrene blocks.

27. The implantable or insertable medical device of claim 26, wherein said polymeric carrier region does not comprise a supplemental silicone polymer.

* * * * *